United States Patent [19]

Kasprzak

[11] Patent Number: 5,443,760
[45] Date of Patent: * Aug. 22, 1995

[54] SILICONE CONTAINING OIL-IN-WATER EMULSIONS

[75] Inventor: Kenneth A. Kasprzak, Saginaw, Mich.

[73] Assignee: Dow Corning Corporation, Midland, Mich.

[*] Notice: The portion of the term of this patent subsequent to Apr. 12, 2011 has been disclaimed.

[21] Appl. No.: 71,734

[22] Filed: Jun. 3, 1993

[51] Int. Cl.$^6$ .................... B01J 13/00; A61K 31/765
[52] U.S. Cl. .................... 424/78.03; 252/302; 252/309; 252/314; 514/847; 514/937; 514/63
[58] Field of Search ............ 252/302, 309, 314; 424/78.03, 184; 514/847, 937

[56] References Cited

U.S. PATENT DOCUMENTS

| | | | |
|---|---|---|---|
| 4,122,029 | 10/1978 | Gee et al. | 252/309 |
| 4,311,695 | 1/1982 | Starch | 424/184 |
| 4,801,447 | 1/1989 | Gum | 514/847 |
| 5,036,108 | 7/1991 | Asahi et al. | 514/937 |
| 5,302,382 | 4/1994 | Kasprzak | 424/78.03 |

*Primary Examiner*—Shean Wu
*Attorney, Agent, or Firm*—James L. DeCesare

[57] ABSTRACT

An oil-in-water emulsion is prepared with certain siloxane-oxyalkylene copolymeric surfactants which have in the emulsion a combined HLB value of between about 4–7. The oil phase includes silicone oils which are volatile and silicone oils or gums which are non-volatile, or mixtures of silicone oils and gums. What is unexpected and unusual about the invention is that conventional wisdom dictates that surfactant packages having a combined HLB value of 4–7 result in water-in-oil emulsions rather than oil-in-water emulsions.

10 Claims, No Drawings

SILICONE CONTAINING OIL-IN-WATER EMULSIONS

BACKGROUND OF THE INVENTION

This invention is directed to oil-in-water emulsions containing silicone surfactants which have a combined HLB value of about 4–7. This is unusual because it is known that emulsions containing surfactants having combined HLB values of 4–7 are water-in-oil emulsions, and not oil-in-water emulsions.

The HLB system is based on the concept that a surfactant molecule has an attraction for both water and oil, and that the relative magnitude or the hydrophile-lipophile balance (HLB), of these attractions measures its suitability as an emulsifier for a given oil. The HLB system is based upon a numerical rating scale of from 0 to 20.

There are two basic types of emulsions, that is, water-in-oil emulsions and oil-in-water emulsions. There is a required HLB value for each type of emulsion. Water-in-oil emulsions require an HLB value of 4–7. Oil-in-water emulsions require an HLB value of 8–18. Generally, no emulsions result with an HLB value below 4 or an HLB value above 18.

Since oil-in-water emulsions require an HLB value of 9–16, it is therefore highly unusual and unexpected that one could prepare an oil-in-water emulsion with HLB value required for water-in-oil emulsions. This is the crux of the present invention.

SUMMARY OF THE INVENTION

The invention relates to an oil-in-water emulsion prepared with certain surfactants which are silicone oxyalkylene copolymers having a combined HLB value of between about 4–7. The oil phase includes silicone oils which are volatile and silicone oils which are non-volatile, or mixtures of silicone oils.

What is unexpected about the present invention is that conventional wisdom dictates that surfactant packages having a combined HLB value of 4–7, result in water-in-oil emulsions rather than oil-in-water emulsions.

The uniqueness of the present invention will become more apparent from a consideration of the following detailed description thereof.

DETAILED DESCRIPTION OF THE INVENTION

The emulsion prepared in accordance with the present invention is an oil-in-water emulsion. The oil phase typically contains a silicone fluid such as a volatile cyclic silicone or a volatile short chain linear silicone, a linear non-volatile silicone, or mixtures of silicone fluids; and an ethylene oxide/propylene oxide silicone copolymer which will be referred to hereinafter as an "EO/PO Silicone Surfactant". The water phase typically contains an ethylene oxide silicone copolymer which will be referred to hereinafter as an "EO Silicone Surfactant"; or the water phase may contain an "EO/PO Silicone Surfactant"; water; and if desired, other adjuvants such as electrolytes and humectants which typically occur in personal care consumer cosmetic products.

The "EO/PO Silicone Surfactant" is a siloxane polyether having the formula:

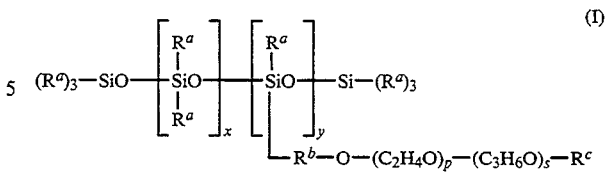

wherein $R^a$ is an alkyl group of one to six carbon atoms; $R^b$ is the radical $-C_mH_{2m}-$; $R^c$ is a terminating radical which can be hydrogen, an alkyl group of one to six carbon atoms, or an aryl group such as phenyl; m has a value of two to eight; p and s have values such that the oxyalkylene segment $-(C_2H_4O)_p-(C_3H_6O)_s-$ has a molecular weight in the range of 400 to 5,000; the segment preferably having fifty to one hundred mole percent of oxyethylene units $-(C_2H_4O)_p-$ and one to fifty mole percent of oxypropylene units $-(C_3H_6O)_s-$; x has a value of 80 to 120; and y has a value of 2 to 10.

Preferably $R^a$ and the terminating radical $R^c$ are methyl groups; m is preferably three or four whereby the group $R^b$ is most preferably the radical $-(CH_2)_3-$; and the values of p and s are such as to provide a molecular weight of the oxyalkylene segment $-(C_2H_4O)_p-(C_3H_6O)_s-$ of between about 1,000 to 3,000. Most preferably p and s should each have a value of about 18 to 28.

The "EO Silicone Surfactant" is a siloxane polyether having the formula:

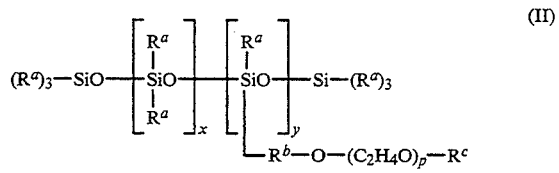

wherein $R^a$ is an alkyl group of one to six carbon atoms; $R^b$ is the radical $-C_mH_{2m}-$; $R^c$ is a terminating radical which can be hydrogen, an alkyl group of one to six carbon atoms, or an aryl group such as phenyl; m has a value of two to eight; p has a value of 8 to 16; x has a value of 6 to 12; and y has a value of 1 to 8.

It should be understood that in both Formulas (I) and (II) shown above, that the siloxane-oxyalkylene copolymers of the present invention may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^a$ substituents which are attached to the two terminal silicon atoms at the end of the siloxane chain can be substituted with the segment $-R^b-O-(C_2H_4O)_p-(C_3H_6O)_s-R^c$ or with the segment $-R^b-O-(C_2H_4O)_p-R^c$. In some instances, it may be desirable to provide the segment $-R^b-O-(C_2H_4O)_p-(C_3H_6O)_s-R^c$ or the segment $-R^b-O-(C_2H_4O)_p-R^c$ at locations which are in the siloxane chain as well as at locations at one or both of the siloxane chain ends.

Methods of making such siloxane-oxyalkylene copolymers are known in the art, and are described in detail for example, in the volume "Chemistry and Technology of Silicones", Walter Noll, Academic Press Inc., 1968, Pages 373–376.

For the sake of brevity, the siloxane polyether of Formula (I) shall be referred to in the examples and in the tables as the "EO/PO Silicone Surfactant A", and the siloxane polyether of Formula (II) shall be referred to as the "EO Silicone Surfactant". It should be understood that where reference is made to "EO/PO Silicone Surfactant A" in the examples and tables, that this material constitutes a mixture containing about thirteen percent by weight of the EO/PO silicone surfactant as active ingredient, and about eighty-seven percent by weight of a volatile cyclic silicone. Reference will also be made to an "EO/PO Silicone Surfactant B" which is essentially the same as "EO/PO Silicone Surfactant A" except that material does not contain the volatile cyclic silicone.

The HLB value of "EO/PO Silicone Surfactant A" is about 1.8. The HLB value of the "EO Silicone Surfactant" is about 13.6. The HLB value of the "EO/PO Silicone Surfactant B" is about 5.9.

The volatile silicone used in the "EO/PO Silicone Surfactant A", and volatile silicone used as a component of the oil phase of the emulsion of the present invention is a low viscosity methylsilicone fluid. These volatile low viscosity methylsilicone fluids correspond to the formula $(CH_3)_aSiO_{(4-a/2)}$ wherein a is an integer having an average value of from two to three. The methylsilicone fluid contains siloxane units joined by Si—O—Si bonds. Representative units are $(CH_3)_3SiO_{1/2}$, $(CH_3)_2SiO_{2/2}$, $(CH_3)SiO_{3/2}$, and $SiO_{4/2}$. These units are present in molar amounts such that there is provided an average of from about two to three methyl groups per silicon atom in the methylsilicone fluid; whereby the methylsilicone fluid has a viscosity of less than about one hundred centistokes measured at twenty-five degrees Centigrade, preferably less than about ten centistokes.

The volatile low viscosity methylsilicone fluid contains dimethylsiloxane units and optionally trimethylsiloxane units. Representative compounds are cyclopolysiloxanes of the formula $[(CH_3)_2SiO]_x$, and linear siloxane compounds of the formula $(CH_3)_3SiO[(CH_3)_2SiO]_ySi(CH_3)_3$, in which x is an integer having a value of from three to ten, and y is an integer having a value of from zero to about four.

The volatile low viscosity methylsilicones have boiling points generally less than about two hundred-fifty degrees Centigrade, and as noted above, preferably possess viscosities less than about ten centistokes. Most preferably, the viscosity is 0.65 to 5.0 centistokes.

The cyclopolysiloxanes have been assigned the adopted name "CYCLOMETHICONE" by The Cosmetics, Toiletries and Fragrance Association, Inc., Washington, D.C. (CTFA). Both the cyclopolysiloxanes and the volatile linear siloxanes are clear fluids which are essentially odorless, nontoxic, nongreasy and nonstinging. Cosmetically, these methylsilicone fluids are nonirritating to skin and exhibit enhanced spreadability and ease of rub-out when applied to the skin. Once applied to the skin, the materials evaporate leaving behind no residue.

Methylsilicone fluids which are operable in accordance with the present invention leave substantially no residue after thirty minutes at room temperature when one gram of the fluid is placed at the center of a No. 1 circular filter paper having a diameter of 185 mm supported at its perimeter in open room atmosphere.

By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative methylsilicone fluids found to be especially useful in accordance with the present invention are hexamethyldisiloxane which has a boiling point of 99.5 degrees Centigrade and the formula $Me_3SiOSiMe_3$;

octamethyltrisiloxane which has a boiling point of 152 degrees Centigrade and the formula $Me_3SiOMe_2SiOSiMe_3$;

hexamethylcyclotrisiloxane which has a boiling point of 133 degrees Centigrade and the formula $[(Me_2)SiO]_3$;

octamethylcyclotetrasiloxane which has a boiling point of 171 degrees Centigrade and the formula $[(Me_2)SiO]_4$; and decamethylcyclopentasiloxane which has a boiling point of 205 degrees Centigrade and the formula $[(Me_2)SiO]_5$.

These methylsilicone fluids may be used alone, or as mixtures in combinations of two or more. Mixtures of the methylsilicone fluids will result in a volatile material having an evaporating behavior different from any one of the individual methylsilicone fluids.

In some instances, it may be desirable to replace one or more of the methyl groups in the methylsilicone fluid with other groups. Thus, there may be substituted alkyl radicals having two to twelve carbon atoms; or aryl radicals having six to ten carbon atoms.

The oil phase of the emulsion may contain a linear non-volatile silicone component which is a polysiloxane film former having a viscosity in excess of 10 and up to twenty-five million centistokes, preferably a range of about 10 to about 20,000 centistokes. A mixture of non-volatile polysiloxanes having relatively higher and relatively lower viscosities may also be employed. Such polysiloxanes contain the repeating unit

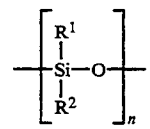

wherein n is an integer having a value greater than 1; $R^1$ is an alkyl radical containing 1 to 7 carbon atoms, or a phenyl group; $R^2$ is an alkyl radical containing 1 to 7 carbon atoms, or a phenyl group. Illustrative polysiloxanes encompassed by the above formula are silicone oils and silicone gums such as polydimethylsiloxane, polydiethylsiloxane, polymethylethylsiloxane, polymethylphenylsiloxane, polydiphenylsiloxanes, and copolymers of two or more of the foregoing siloxanes.

In addition, it may be desirable to include in the oil or water phase of the emulsion other compatible materials such as waxes; sunscreen agents; vitamins such as Vitamin A, Vitamin B, Vitamin D, Vitamin E, ascorbic acid, and biotin; hormones; amino acids; antioxidants such as propyl, octyl, and dodecyl esters of gallic acid, butylated hydroxytoluene, butylated hydroxyanisole (BHA), and natural mixed tocopherols; opacifiers such as titanium dioxide and fatty alcohols; and solvents such as ethanol and isopropanol.

Waxes which may be employed include carnauba, beeswax, ceresin, paraffin, candelilla, bayberry, montan, spermaceti, castor wax, ozokerite, microcrystalline waxes, and Fisher-Tropsch waxes.

Ester waxes may also be employed such as those products sold by Scrota Surfactants, Ltd., North Humberside, England, under the tradename SYN-CHROWAX AW1, BB, BE, BSE14, ERL, HGL, HR, HRS, RLS, and SE.

Colorants include any of the United States Government Food & Drug Administration (FDA) certified inorganic and organic dyes and lakes such as carmine, iron oxide, mica, titanium dioxide, ultramarines, zinc oxide, bismuth oxychloride; and D & C Blue No. 1, D & C Orange No. 5, D & C Red No. 6 Aluminum Lake, D & C Red No. 7 Calcium Lake, D & C Green No. 8, D & C Red No. 17, FD & C Blue No. 1, FD & C Red No. 3, FD & C Yellow No. 6, External D & C Violet No. 2, which are the CTFA adopted names of The Cosmetic, Toiletry, and Fragrance Association, Washington, D.C.

Preservatives which may be used are methyl paraben, ethyl paraben, propyl paraben, butyl paraben, diazolidinyl urea, imidazolidinyl urea, and mixtures thereof. Where an antimicrobial is required, materials such as Triclosan, Quaternium-15, chloroxylenol, and cetyl trimethyl ammonium bromide, may be employed.

An acid may be used to adjust the pH to within the range of three to nine, preferably six to eight. Any water soluble acid such as a carboxylic acid or a mineral acid can be employed. Acids which may be used include mineral acids such as hydrochloric, sulfuric, and phosphoric acid; monocarboxylic acids such as acetic, lactic, and propionic acid; and polycarboxylic acids such as succinic, adipic, salicylic and citric acid.

Suitable neutralizing agents include sodium hydroxide, potassium hydroxide, ammonium hydroxide, monoethanolamine, diethanolamine, and triethanolamine.

Among the numerous humectants which may be employed are polyhydroxy alcohols such as sorbitol, glycerin, hexylene glycol, propylene glycol, and hexanetriol; sugar and starch derivatives such as alkoxylated glucose, and hydrolyzed mucopolysaccharides; D-panthenol, hyaluronic acid, lactamide monoethanolamine, acetamide monoethanolamine, urea, guanidine, glycolic acid and glycolate salts, lactic acid and lactate salts; and mixtures thereof.

Emollient oils which can be employed in the present invention include mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, butyl stearate, cetyl stearate, diisopropyl adipate, isodecyl oleate, diisopropyl sebacate, and lauryl lactate; fatty acids such as lauric, myristic, palmitic, stearic, oleic, linoleic, and behenic, acid; fatty alcohols such as lauryl, myristyl, cetyl, stearyl, isostearyl, oleyl, ricinoleyl, erucyl, and 2-octyl dodecanol, alcohols; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; and hydrocarbons such as petrolatum and squalane. Sunscreen agents may be included in some instances, and can be used in the amount which is within the restricted limits or less as established by the United States Government Food & Drug Administration (FDA). Representative sunscreen agents or mixtures of such agents which may be used include 4-aminobenzoic acid; homomethyl salicylate; 2-hydroxy-4-methoxy benzophenone; 2-phenylbenzimidazol-5-sulfonic acid; 4-dimethylamino benzoic acid 2-ethylhexyl ester; 4-methoxy cinnamic acid isoamyl ester; 4-methoxy cinnamic acid 2-ethylhexyl ester; 3-(4'-methyl) benzylidene-bornane-2-one; 1-(4'-isopropylphenyl)-3-phenyl-1-propane-1,3-dione; and 1-(4'-t-butylphenyl)-3-(4-methoxyphenyl)-propane-1,3-dione.

Fragrances which may be used include natural products such as ambergris, benzoin, civet, clove, leaf oil, jasmine, mate', mimosa, musk, myrrh, orris, sandalwood oil and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Thickening agents which may be used include polyacrylates; sodium alginate; gum arabic; guar gum; carboxyvinyl polymers; cellulose derivatives such as methylcellulose, ethyl cellulose, hydroxypropyl methylcellulose, hydroxyethylcellulose, hydroxypropylcellulose, and carboxymethylcellulose; starch and starch derivatives such as hydroxyethylamylose and starch amylose; polyvinyl alcohol; locust bean gum; vegetable gums; magnesium aluminum silicate such as Veegum, a tradename of R. T. Vanderbilt Company, Incorporated, Norwalk, Conn. saccharide and saccharide derivatives such as fructose, glucose, and PEG-120 methyl glucose dioleate; and any of the various organically modified montmorillonite clays sold under the trademark BENTONE® by Rheox Incorporated, Highstown, N.J., such as BENTONE® 38.

Divalent and trivalent salts may be used as electrolytes, and suitable salts are sodium chloride, magnesium chloride, aluminum chloride, and ammonium chloride. Sodium borate may also be employed, as well as certain antiperspirant salts such as aluminum chlorohydrate and aluminum-zirconium chlorohydrate. These electrolytes and salts aid in reducing the particle size of the silicone in the emulsion which has a net thickening effect.

The invention is illustrated in more detail in the following examples and tables.

EXAMPLE I

Oil-in-water emulsions were prepared by separately forming an oil phase in one four hundred milliliter beaker, and a water phase in another four hundred milliliter beaker. An electric mixer was placed in each beaker and used until each phase in each beaker was uniform. The oil phase was slowly added from one beaker to the water phase in the other beaker while agitating the combined phases with the electric mixer. The two phases were mixed together for about ten minutes. The mixed phases were placed on an EPPENBACH mixer which was set at forty on the variable speed control. The phases were mixed on the EPPENBACH mixer for about ten minutes. The resulting mixture was placed into an eight ounce bottle. Tables I–III appearing below show the ingredients used to prepare each phase of each of the oil-in-water emulsions.

TABLE I

| Ingredient | Emulsion 1 Weight % | Emulsion 2 Weight % | Emulsion 3 Weight % |
|---|---|---|---|
| OIL PHASE | | | |
| Volatile cyclic silicone | 15.0 | 15.0 | 15.0 |
| Non-Volatile Linear silicone (10 cs.) | 5.0 | 5.0 | 5.0 |
| EO/PO Silicone Surfactant A | 8.0 | 8.0 | 8.0 |
| WATER PHASE | | | |
| EO/PO Silicone Surfactant B | — | 1.0 | 2.0 |
| EO Silicone Surfactant | 0.5 | — | — |
| Water | 61.5 | 61.0 | 60.0 |
| Sodium chloride | 2.0 | 2.0 | 2.0 |
| Propylene glycol | 8.0 | 8.0 | 8.0 |
| Combined HLB | 6.3 | 4.1 | 4.7 |

TABLE II

| Ingredient | Emulsion 4 Weight % | Emulsion 5 Weight % | Emulsion 6 Weight % |
|---|---|---|---|
| OIL PHASE | | | |
| Volatile cyclic silicone | 19.0 | 19.0 | 30.0 |
| Non-Volatile Linear silicone (10 cs.) | 5.0 | 5.0 | 5.0 |
| EO/PO Silicone Surfactant A | 4.0 | 4.0 | 8.0 |
| WATER PHASE | | | |
| EO/PO Silicone Surfactant B | 0.5 | 2.0 | — |
| EO Silicone Surfactant | — | — | 0.5 |
| Water | 61.5 | 60.0 | 46.5 |
| Sodium chloride | 2.0 | 2.0 | 2.0 |
| Propylene glycol | 8.0 | 8.0 | 8.0 |
| Combined HLB | 4.1 | 5.2 | 6.3 |

TABLE III

| Ingredient | Emulsion 7 Weight % | Emulsion 8 Weight % | Emulsion 9 Weight % |
|---|---|---|---|
| OIL PHASE | | | |
| Volatile cyclic silicone | 30.0 | 45.0 | 45.0 |
| Non-Volatile Linear silicone (10 cs.) | 5.0 | 5.0 | 5.0 |
| EO/PO Silicone Surfactant A | 8.0 | 8.0 | 8.0 |
| WATER PHASE | | | |
| EO/PO Silicone Surfactant B | 2.0 | — | 2.0 |
| EO Silicone Surfactant | — | 0.5 | — |
| Water | 45.0 | 31.5 | 30.0 |
| Sodium chloride | 2.0 | 2.0 | 2.0 |
| Propylene glycol | 8.0 | 8.0 | 8.0 |
| Combined HLB | 4.7 | 6.3 | 4.7 |

The combined HLB value of the silicone surfactant system of each of the foregoing oil-in-water emulsions was calculated by multiplying the ratio of each of the individual silicone surfactants in each emulsion to the total surfactant content in each emulsion by its individual HLB number, and combining the two values. The combined HLB value of each of the oil-in-water emulsions is shown in Tables I–III. The oil-in-water emulsions formed in accordance with the present invention possess utility in personal care cosmetic products intended for application to the human skin.

These emulsions preferably contain from 0.1 to 60.0 percent by weight of silicone oil or silicone gum; 40.0 to 90.0 percent by weight of water; 0.5 to 5.0 percent by weight of the silicone surfactants; and 0.35 to 25.0 percent by weight of an electrolyte.

Other variations and modifications may be made in the compounds, compositions, and methods described herein without departing from the essential features and concepts of the present invention. The forms of the invention described herein are exemplary only and are not intended as limitations on the scope of the invention which is defined in the appended claims.

That which is claimed is:

1. A method of making an emulsion comprising (i) preparing an oil phase having a silicone oil and a first silicone oxyalkylene copolymer; (ii) preparing an aqueous phase having water and a second silicone oxyalkylene copolymer; the combined hydrophile-lipophile balance (HLB) of the first and second silicone oxyalkylene copolymers having a value in the range of 4 to 7; and (iii) forming an oil-in-water emulsion by adding the oil phase to the aqueous phase and mixing the phases.

2. A method according to claim 1 in which the silicone oil in the oil phase is a mixture which includes a volatile cyclopolysiloxane having the formula $[(CH_3)_2SiO]_x$ in which x has a value of 3 to 10, and a non-volatile linear polysiloxane having a viscosity of 10 to 10,000 centistokes.

3. A method according to claim 2 in which the first silicone oxyalkylene copolymer in the oil phase is a siloxane polyether of the formula:

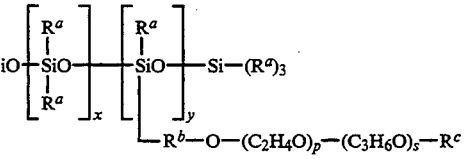

wherein $R^a$ is an alkyl group of one to six carbon atoms; $R^b$ is the radical $-C_mH_{2m}-$; $R^c$ is a terminating radical selected from the group consisting of hydrogen, an alkyl group of one to six carbon atoms, and an aryl group; m has a value of two to eight; p and s each have values between 18 to 28; x has a value of 80 to 120; and y has a value of 2 to 10.

4. A method according to claim 3 in which the second silicone oxyalkylene copolymer in the aqueous phase is a siloxane polyether of the formula:

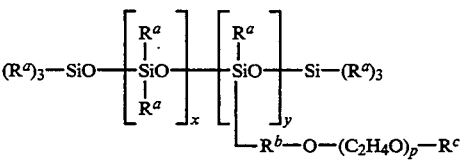

wherein $R^a$ is an alkyl group of one to six carbon atoms; $R^b$ is the radical $-C_mH_{2m}-$; $R^c$ is a terminating radical selected from the group consisting of hydrogen, an alkyl group of one to six carbon atoms, or an aryl group; m has a value of two to eight; p has a value of 8 to 16; x has a value of 6 to 12; and y has a value of 1 to 8.

5. A method according to claim 3 in which the second silicone oxyalkylene copolymer in the aqueous phase is a siloxane polyether of the formula in accordance with claim 3.

6. A method according to claim 3 in which the combined hydrophile-lipophile balance (HLB) of the first and second silicone oxyalkylene copolymers has a value of between 6 and 7.

7. A method of making an emulsion comprising (i) preparing an oil phase having a silicone oil and a first silicone oxyalkylene copolymer; (ii) preparing an aqueous phase having water and a second silicone oxyalkylene copolymer; the combined hydrophile-lipophile balance (HLB) of the first and second silicone oxyalkylene copolymers having a value in the range of 4 to 7; and (iii) forming an oil-in-water emulsion by adding the oil phase to the aqueous phase and mixing the phases; the silicone oil in the oil phase being a mixture which includes a volatile cyclopolysiloxane of the formula $[(CH_3)_2SiO]_x$ in which x has a value of 3 to 10, and a non-volatile linear polysiloxane having a viscosity of 10 to 10,000 centistokes; the first silicone oxyalkylene copolymer in the oil phase being a siloxane polyether of the formula:

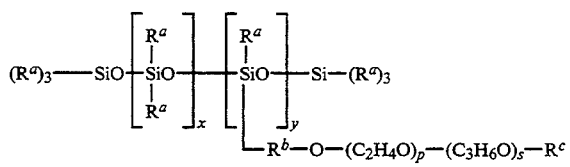

wherein $R^a$ is an alkyl group of one to six carbon atoms; $R^b$ is the radical $—C_mH_{2m}—$; $R^c$ is a terminating radical selected from the group consisting of hydrogen, an alkyl group of one to six carbon atoms, and an aryl group; m has a value of two to eight; p and s each have values between 18 to 28; x has a value of 80 to 120; and y has a value of 2 to 10; and the second silicone oxyalkylene copolymer in the aqueous phase being a siloxane polyether of the formula:

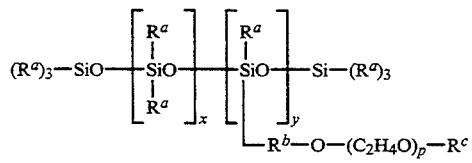

wherein $R^a$ is an alkyl group of one to six carbon atoms; $R^b$ is the radical $—C_mH_{2m}—$; $R^c$ is a terminating radical selected from the group consisting of hydrogen, an alkyl group of one to six carbon atoms, or an aryl group; m has a value of two to eight; p has a value of 8 to 16; x has a value of 6 to 12; and y has a value of 1 to 8.

8. A method of making an emulsion comprising (i) preparing an oil phase having a silicone oil and a first silicone oxyalkylene copolymer; (ii) preparing an aqueous phase having water and a second silicone oxyalkylene copolymer; the combined hydrophile-lipophile balance (HLB) of the first and second silicone oxyalkylene copolymers having a value in the range of 4 to 7; and (iii) forming an oil-in-water emulsion by adding the oil phase to the aqueous phase and mixing the phases; the silicone oil in the oil phase being a mixture which includes a volatile cyclopolysiloxane of the formula $[(CH_3)_2SiO]_x$ in which x has a value of 3 to 10, and a non-volatile linear polysiloxane having a viscosity of 10 to 10,000 centistokes; the first silicone oxyalkylene copolymer in the oil phase and the second silicone oxyalkylene copolymer in the aqueous phase each being a siloxane polyether of the formula:

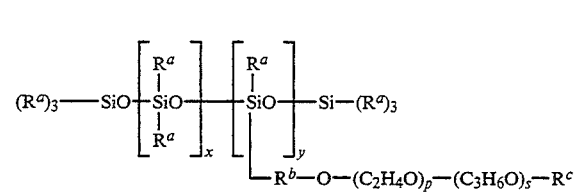

wherein $R^a$ is an alkyl group of one to six carbon atoms; $R^b$ is the radical $—C_mH_{2m}—$; $R^c$ is a terminating radical selected from the group consisting of hydrogen, an alkyl group of one to six carbon atoms, and an aryl group; m has a value of two to eight; p and s each have values between 18 to 28; x has a value of 80 to 120; and y has a value of 2 to 10.

9. An oil-in-water emulsion made by a method comprising (i) preparing an oil phase having a silicone oil and a first silicone oxyalkylene copolymer; (ii) preparing an aqueous phase having water and a second silicone oxyalkylene copolymer; the combined hydrophile-lipophile balance (HLB) of the first and second silicone oxyalkylene copolymers having a value in the range of 4 to 7; and (iii) forming an oil-in-water emulsion by adding the oil phase to the aqueous phase and mixing the phases.

10. A cosmetic product comprising an emulsion made by (i) preparing an oil phase having a silicone oil and a first silicone oxyalkylene copolymer; (ii) preparing an aqueous phase having water and a second silicone oxyalkylene copolymer; the combined hydrophile-lipophile balance (HLB) of the first and second silicone oxyalkylene copolymers having a value in the range of 4 to 7; and (iii) forming an oil-in-water emulsion by adding the oil phase to the aqueous phase and mixing the phases.

* * * * *